(12) United States Patent
Bergeron et al.

(10) Patent No.: US 6,706,679 B1
(45) Date of Patent: Mar. 16, 2004

(54) USE OF COPOLYMERS ON THE BASIS OF UNSATURATED ACIDS OR THEIR DERIVATIVES AS FOAM-PROTECTING AGENT

(75) Inventors: Vance Bergeron, Lyons (FR); Harold Schoonbrood, Fitzroy North (AU)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/600,389

(22) PCT Filed: Jan. 19, 1999

(86) PCT No.: PCT/FR99/00091

§ 371 (c)(1),
(2), (4) Date: Jul. 14, 2000

(87) PCT Pub. No.: WO99/36496

PCT Pub. Date: Jul. 22, 1999

(30) Foreign Application Priority Data

Jan. 13, 1998 (FR) .............................................. 98 00518
Jan. 19, 1998 (FR) .............................................. 98 00693

(51) Int. Cl.[7] .............................. C11D 3/37; A61K 7/48
(52) U.S. Cl. ...................... 510/476; 510/361; 510/434; 510/475; 510/477; 424/70.11; 424/78.18; 424/401
(58) Field of Search ................................ 510/361, 434, 510/475, 476, 477; 424/70.11, 78.18, 401

(56) References Cited

U.S. PATENT DOCUMENTS

| | | | | |
|---|---|---|---|---|
| 4,664,835 A | | 5/1987 | Grollier | ........................ 252/90 |
| 4,814,102 A | * | 3/1989 | Baur et al. | ............. 252/174.24 |
| 4,874,540 A | * | 10/1989 | Greenwald et al. | .... 252/174.24 |
| 4,956,421 A | * | 9/1990 | Denzinger et al. | .......... 525/385 |
| 5,318,719 A | * | 6/1994 | Hughes et al. | ......... 252/174.23 |
| 5,423,999 A | * | 6/1995 | Egraz et al. | ................. 252/140 |
| 5,538,663 A | * | 7/1996 | Kihara et al. | ............... 510/395 |
| 5,686,024 A | * | 11/1997 | Dahanayake et al. | ....... 252/356 |
| 5,830,956 A | * | 11/1998 | Stockhausen et al. | .... 526/318.2 |

FOREIGN PATENT DOCUMENTS

| | | | | |
|---|---|---|---|---|
| DE | 44 15 804 | | 11/1995 | ............. C11D/1/83 |
| EP | 639592 | * | 2/1995 | ......... C08F/283/06 |
| FR | 2 603 802 | | 3/1988 | ............. A61K/7/48 |
| FR | 2 731 616 | | 9/1996 | ............. A61K/7/48 |
| FR | 2 737 660 | | 2/1997 | ............. A61K/7/11 |
| WO | Wo94 26238 | | 11/1994 | ............. A61K/7/06 |
| WO | WO 97 22640 | | 6/1997 | ......... C08F/220/28 |

OTHER PUBLICATIONS

International Search Report Apr. 21, 1999.

* cited by examiner

*Primary Examiner*—Brian P. Mruk

(57) ABSTRACT

The invention relates to the use of a copolymer or a mixture of copolymers as foam-protecting agents in detergent or cosmetic formulations, comprising at least one monomer (I) selected from the acids, diacids or unsaturated C3–C5 anhydrides; or at least one monomer (II) selected from ethylene oxide and propylene oxide; or at least one monomer (III) selected from the linear or branched C4–C8 hydrocarbons, comprising at least one ethenoid unsaturation; or at least one monomer (IV) of formula R1 —COO—R2, where R1 is a possibly substituted linear or branched C1–C3 hydrocarbon radical; R2 is a linear or branched C1–C4 hydrocarbon radical which is possibly substituted by an anionic radical or a hydroxyl group; and the monomer (IV) further comprises at least one ethenoid unsaturation.

7 Claims, No Drawings

USE OF COPOLYMERS ON THE BASIS OF UNSATURATED ACIDS OR THEIR DERIVATIVES AS FOAM-PROTECTING AGENT

This application is an application under 35 U.S.C. Section 371 of International Application Number PCT/FR99/00091 filed on Jan. 19, 1999.

The present invention relates to copolymers in which one of the monomers is an unsaturated acid or diacid, or a derivative, as a foam protector in detergent or cosmetic formulations.

The appearance of a large amount of long-lasting foam is a phenomenon which is very important to have in detergent or cosmetic formulations, more particularly those which are used by hand. The reason for this is that it is clearly recognized that this foaming phenomenon is synonymous, for the user, with the efficacy of the cleaning undertaken. Consequently, even though this phenomenon does not really have any effect on the quality of the cleaning, a particular objective of formulators is to prepare formulations which give a large amount of foam.

However, the appearance and especially the durability of the foam are highly dependent on the other compounds present in the bath, and mainly greases. In other words, once the washing bath contains greasy substances, the foam is more or less rapidly eliminated.

One aim of the present invention is to propose detergent and cosmetic formulations which generate large amounts of foam, and especially which conserve this foam, in particular under unfavorable conditions, such as in the presence of greases, and possibly of divalent cations such as calcium.

Thus, a subject of the present invention is the use, as a foam protector in detergent or cosmetic formulations, of a copolymer or a mixture of copolymers comprising:
- at least one monomer (I) chosen from $C_3$–$C_5$ unsaturated acids, diacids or anhydrides, or
- at least one monomer (II) chosen from ethylene oxide and propylene oxide, or
- at least one monomer (III) chosen from linear or branched $C_4$–$C_8$ hydrocarbons comprising at least one ethylenic unsaturation, or
- at least one monomer (IV) of the following formula:

$$R^1\text{—COO—}R^2,$$

in which:
- $R^1$ represents a linear or branched, optionally substituted $C_1$–$C_4$ hydrocarbon-based radical;
- $R^2$ represents a linear or branched $C_1$–$C_4$ hydrocarbon-based radical optionally substituted with an anionic group which can be in the form of an acid or of an alkali metal salt or ammonium salt of —$N(R^3)_3^+$ type, with $R^3$, which may be identical or different, representing hydrogen atoms or $C_1$–$C_4$ hydrocarbon-based radicals, or optionally substituted with a hydroxyl group;
- the monomer (IV) comprising at least one ethylenic unsaturation.

It should be noted that the term "foam protector" means a compound which conserves this foam, at least partly, under unfavorable conditions, such as in the presence of greases or of divalent cations. It should be noted that the foamability of the polymer used as a foam protector in the present invention is not a criterion that is considered as truly essential. However, the compound used should not excert a harmful effect on the ability of the foaming agents moreover present in the formulation.

The term "greases" refers more particularly to any liquid and/or solid hydrophobic hydrocarbon-based medium having, for example, a solubility in water of less than 5 g/l, preferably less than 1 g/l.

This grease can be provided by the external medium and/or can be a constituent of the detergent or cosmetic formulation. Thus, it can be either a hydrophobic soiling or a hydrophobic active compound of said formulation, for example.

Greases which may be mentioned as examples are:
- aliphatic or aromatic hydrocarbons (alkanes (for example such as hexadecane), paraffins, mineral oils, liquid paraffins, kerosene, petrol, fuel, perhydrosqualane, squalene, etc.);
- alkylmonoglycerides, alkyldiglycerides, triglycerides, such as the oils extracted from plants and vegetation (palm oil, coconut oil, cotton seed oil, soybean oil, sunflower oil, olive oil, grape seed oil, sesame oil, ground nut oil, castor oil, hazlenut oil, etc.) or oils of animal origin—tallow, fish oils), derivatives of these oils such as hydrogenated oils, and lanolin derivatives;
- natural or non-natural essential oils, such as eucalyptus oil, lavender oil, hybrid lavender oil, vetiver oil, lemon oil, orange oil, sandalwood oil, rosemary oil, camomile oil, savory oil, nutmeg oil, cinnamon oil, bergamot oil, cade oil, geraniol oil, etc.,
- fatty alcohols such as cetyl alcohol, stearyl alcohol or oleyl alcohol;
- fatty esters such as isopropyl palmitate, 2-ethylhexyl cocoate, myristyl myristate, lactic acid esters, stearic acid esters, behenic acid esters, or isostearic acid esters;
- polyorganosiloxane oils, gums or resins such as linear or cyclic polydimethylsiloxanes, $\alpha,\omega$-hydroxylated polydimethylsiloxanes, $\alpha,\omega$-trimethylsilyl polydimethylsiloxanes, polyalkylmethylsiloxanes, polymethylphenylsiloxanes, polydiphenylsiloxanes, amino derivatives of silicones and silicone waxes;
- organic soiling (sebum, etc.).

Thus, the use of these copolymers in detergent or cosmetic formulations gives initial foaming properties that are at least as good as those of conventional formulations. In addition, and this constitutes a noteworthy advantage of these copolymers, the use of these copolymers in detergent and cosmetic formulations makes it possible to conserve a foam volume which is 10%, preferably 15% or even up to 30% greater than that of formulations from which they are absent, and allows this in the presence of greases possibly combined with divalent cations.

However, other aims and advantages of the present invention will emerge more clearly on reading the description and the examples which follow.

As has just been stated, the foam protector used in the present invention is a copolymer or a mixture of several copolymers comprising at least one of the monomers (I) to (IV) mentioned previously.

More specifically, the copolymer or mixture of copolymers comprises at least one monomer of at least two monomers of types (I) to (IV), of at least two monomers of the type (IV) and optionally of at least one monomer of type (I) to (III), or mixtures thereof.

It should be noted that the copolymer used as foam protector is more particularly soluble at the time of use of the formulation into which it is introduced, i.e. soluble in aqueous media.

More particularly, the copolymer is such that it is soluble in an aqueous solution of basic pH. Such conditions are conventional in particular in the washing up of kitchenware and in the washing of laundry.

In addition, the copolymer used according to the invention advantageously has both a hydrophilic part and a hydrophobic part. Thus, it lowers the interface tension between the aqueous solution and the greases, which improves the dispersion of these greases in the aqueous solution.

Generally, the copolymers used according to the invention have a weight-average molar mass of between $10^3$ and $10^7$ g/mol, more particularly between $10^4$ and $10^6$ g/mol and preferably between $10^4$ and $5 \times 10^5$ g/mol. According to an even more advantageous embodiment, the copolymers have a weight-average molar mass of between $1.5 \times 10^4$ and $5 \times 10^5$ g/mol. The molar mass is determined by steric exclusion chromatography in aqueous phase. As an example of a method for measuring the molar mass of the copolymers used in the context of the invention, a TSK-gel column, with an eluent comprising water, 0.1 mol/l of $NaO_3$ and 200 ppm of $NaN_3$, was used. The detection of the molar mass is based on the refractive index, using polyethylene oxide as standard.

As more particularly regards the monomer (I), this monomer is chosen from $C_3$–$C_5$ unsaturated acids, diacids or anhydrides.

The most suitable representatives of these monomers are acrylic acid and methacrylic acid. As regards the diacids and anhydrides, mention may be made, inter alia, of maleic acid, fumaric acid, itaconic acid, maleic anhydride, furmaric anhydride and itaconic anhydride.

The monomer (II) is chosen from ethylene oxide and propylene oxide.

The monomer (III) is chosen from linear or branched hydrocarbons comprising at least one $C_4$–$C_8$ ethylenic unsaturation. As examples of monomers of this type, mention may be made most particularly of isobutylene and diisobutylene.

Finally, the monomer (IV) corresponds to the following formula:

$R^1$—COO—$R^2$, in which:

$R^1$ represents a linear or branched, optionally substituted $C_1$–$C_4$ hydrocarbon-based radical;

$R^2$ represents a linear or branched $C_1$–$C_4$ hydrocarbon-based radical, optionally substituted with an anionic radical which can be in the form of an acid or of an alkali metal salt or ammonium salt of —$N(R^3)_3^+$ type, with $R^3$, which may be identical or different, representing hydrogen atoms or $C_1$–$C_4$ hydrocarbon-based radicals, or optionally substituted with a hydroxyl group;

the monomer (IV) comprising at least one ethyleneic unsaturation.

More particularly, said monomer (IV) is such that $R^1$ is derived from acrylic acid, methacrylic acid or acetic acid.

It can also be envisaged to use a monomer (IV) whose radical $R^1$ is substituted. It should be noted that the term "substituent" means a pendant radical or a group which interrupts the hydrocarbon-based chain. Thus, suitable substituents which may be mentioned are the radicals —OH, —O—, —C(O)—, —C(O)—N— and —C(O)OR, with R representing a hydrogen atom, an alkali metal or a $C_1$–$C_4$ hydrocarbon-based radical, which is preferably saturated.

The expression "anionic radical" is intended to denote sulfone, sulfate, phosphate, phosphonate and carboxylic radicals. A sulfone monomer is preferably used.

According to one specific embodiment of the invention, the monomer (IV) comprises at least one ethylenic unsaturation. If there is only one unsaturation, it can be either on the radical $R^1$ or on the radical $R^2$. If there are several unsaturations, they can be on the radical $R^1$, on the radical $R^2$ or on both the radicals $R^1$ and $R^2$.

A monomer comprising only one ethylenic unsaturation is preferably used.

Consequently, if the monomer (IV) is derived from an acid bearing an unsaturation, then the radical $R^2$ does not bear any ethylenic unsaturation. On the other hand, in the opposite case, the radical $R^2$ comprises the ethylenic unsaturation.

A first embodiment of the invention consists of the use of a copolymer comprising at least one monomer (I) and at least one monomer (III).

This copolymer preferably comprises maleic acid or maleic anhydride as monomer (I) and isobutylene or diisobutylene as monomer (III).

The copolymer can be in the acid form or in the form of an alkali metal salt or ammonium salt of —$N(R^3)_3^+$ type, with $R^3$, which may be identical or different, representing hydrogen atoms or $C_1$–$C_4$ hydrocarbon-based radicals. Preferably, the copolymer is in the form of sodium salts.

The monomers are distributed alternately in the molecule.

The proportion of the monomer (I) relative to the monomer (III) is 50/50.

These copolymers are well-known compounds and are sold in particular under the name Geropon® T 36 (Rhodia Chimie).

A second embodiment of the invention consists of the use of a copolymer comprising at least one monomer (I) and at least one monomer (II).

This copolymer more particularly comprises a polymer chain consisting of the monomer(s) (II) onto which are grafted polymer chains derived from the monomer(s) (I).

According to one particularly advantageous variant of the invention, said copolymer comprises acrylic acid as monomer (I), and ethylene oxide or an ethylene oxide/propylene oxide mixture as monomer (II). In the case of an ethylene oxide/propylene oxide mixture, a chain containing an ordered distribution, corresponding to a dibloc of the two abovementioned monomers, is preferably used.

The copolymer according to this variant has a weight proportion of monomer (II) ranging from 1 to 50% relative to the weight of the copolymer. Preferably, it is between 1 and 30% relative to the weight of the copolymer.

These copolymers can be obtained by any means known to those skilled in the art.

For example, they are obtained by carrying out a polymerization, in a suitable solvent, of the monomer (I) and of the polymer chain consisting either of ethylene oxide alone or of an ethylene oxide/propylene oxide mixture, in the presence of an initiator for generating free radicals. The reaction is generally carried out using water or an alcohol/water mixture. In addition, the polymerization reaction is carried out in the presence of a base, such that, if it is present, the monomer (I) is partially neutralized.

According to a third embodiment of the invention, the copolymer used as foam protector optionally comprises at least one monomer (I) and at least one monomer (IV).

The monomer (IV) can be chosen more particularly from the following monomers: vinyl acetate; alkyl acrylate; alkyl methacrylate; alkyl methacrylate or acrylate bearing, as anionic group, a sulfonated (sulfoalkyl) group, in the form of an acid or of an alkali metal salt or ammonium salt of —$N(R^3)_3^+$ type; hydroxyalkyl acrylate or methacrylate;

monomers in which the alkyl radical corresponds to methyl, ethyl, propyl and propyl isomer, butyl and butyl isomer radicals.

As regards the sulfonated monomers, monomers in salt form are more particularly used, preferably in the form of an alkali metal salt. Examples of monomers of sulfoalkyl type which may be mentioned are sodium sulfoethyl acrylate and sodium sulfoethyl methacrylate.

As regards the monomer comprising a hydroxyalkyl group, 2-hydroxyethyl acrylate and 2-hydroxyethyl methacrylate are advantageous examples.

It should be noted that the copolymer can comprise one or more monomers (IV), with or without monomer (I).

A first type of particularly advantageous copolymer has the following composition:

| | |
|---|---|
| monomer (I) | 0–50% by weight |
| monomer (IV): vinyl acetate | 0–92% by weight |
| $C_1$–$C_4$ alkyl (preferably butyl) (meth)acrylate | 0–50% by weight |
| sodium $C_1$–$C_4$ sulfoalkyl (preferably sulfoethyl) (meth)acrylate | 0–10% by weight | the sum of each of the monomers used being equal to 100% relative to the weight of the copolymer.

This copolymer more particularly comprises 1–15% of monomer (I); 50–85% of vinyl acetate; 5–20% of alkyl acrylate or methacrylate; 0.5–5% of sodium sulfoalkyl acrylate or methacrylate; the sum of each of the monomers used being equal to 100% relative to the weight of the copolymer.

When the copolymer comprises at least one monomer (I), this monomer is chosen more particularly from acrylic acid and methacrylic acid.

A second type of very advantageous copolymer consists in using a monomer (I), and preferably (meth)acrylic acid, and one at least one monomer (IV) comprising a hydroxyl substituent, which is preferably a 2-hydroxyalkyl acrylate or 2-hydroxyalkyl methacrylate, in which the alkyl radical is $C_1$–$C_4$, preferably $C_2$. The proportion of monomer (I) relative to the monomer (IV) is between 0.1 and 90% by weight relative to the weight of the copolymer.

The proportion of monomer (I) in this second type of copolymer is more particularly 0.1–50% by weight relative to the weight of the copolymer, preferably 20–60% by weight.

The copolymers used in this third embodiment of the invention are preferably copolymers with a random distribution of the various monomers mentioned above.

These copolymers can be obtained in this case also by implementing means that are conventional for those skilled in the art.

Thus, the polymerization can take place in solution or in emulsion, by introducing the various monomers in the presence of a compound for generating free radicals. The reaction is generally carried out using water or an alcohol/water mixture. It is possible to carry out the polymerization reaction in solution or in emulsion, in which case it is necessary to use a surfactant. Furthermore, common compounds can be used, if necessary, such as buffers, bases to neutralize the acids, if such monomers are present, and transfer agents (for limiting the growth of the chains).

The foam protector is thus used in detergent or cosmetic formulations, and it represents more particularly 0.05 to 10% by weight of the formulation, more particularly between 0.05 and 2% by weight. The amount of foam protector advantageously represents 0.5 to 2% by weight of the formulation.

The detergent formulations in which the foam protector can be used are more especially household detergent formulations intended for washing up kitchenware by hand or washing laundry by hand.

In the field of household detergency, the present invention is directed more particularly toward liquid compositions for washing up kitchenware by hand.

Said compositions, besides the foam protector according to the invention, can contain from about 0.5 to about 40% by weight of anionic surfactants, from about 0.5 to about 10% by weight of nonionic surfactants and 0 to 20% by weight of zwitterionic or amphoteric surfactants.

ANIONIC SURFACTANTS alkyl sulfates of formula $ROSO_3M$, in which R represents a $C_{10}$–$C_{24}$, preferably $C_{12}$–$C_{20}$ and most particularly $C_{12}$–$C_{18}$, alkyl radical or hydroxyalkyl radical, M representing a hydrogen atom or a cation of the same definition as above, as well as the ethoxylated (EO) and/or propoxylated (PO) derivatives thereof, containing on average from 0.5 to 6 and preferably from 0.5 to 3 EO and/or PO units;

alkyl ether sulfates;

alkylglycoside sulfates;

alkylamide sulfates of formula $RCONHR'OSO_3M$ in which R represents a $C_2$–$C_{22}$, preferably $C_6$–$C_{20}$, alkyl radical, R' represents a $C_2$–$C_3$ alkyl radical, M representing a hydrogen atom or a cation of the same definition as above, as well as the ethoxylated (EO) and/or propoxylated (PO) derivatives thereof, containing on average 0.5 to 60 EO and/or PO units;

$C_9$–$C_{20}$ alkylaryl sulfonates, primary or secondary $C_8$–$C_{22}$ alkyl sulfonates, alkylglyceryl sulfonates, the sulfonated polycarboxylic acids described in GB-1 082 179, sulfonated fatty acid derivatives; paraffin sulfonates;

alkyl ester sulfonates of formula $R—CH(SO_3M)—COOR'$, in which R represents a $C_8$–$C_{20}$, preferably $C_{10}$–$C_{16}$, alkyl radical, R' represents a $C_1$–$C_6$, preferably $C_1$–$C_3$, alkyl radical and M represents an alkali metal (sodium, potassium or lithium) cation, substituted or unsubstituted ammonium (methyl-, dimethyl-, trimethyl- or tetramethylammonium, dimethylpiperidinium, etc.) or an alkanolamine derivative (monoethanolamine, diethanolamine, triethanolamine, etc.). Mention may be made most particularly of methyl ester sulfonates in which the radical R is $C_{14}$–$C_{16}$;

alkyl phosphates;

polyethoxycarboxylates; the cation being an alkali metal (sodium, potassium or lithium), a substituted or unsubstituted ammonium residue (methyl-, dimethyl-, trimethyl- or tetramethylammonium, dimethylpiperidinium, etc.) or an alkanolamine derivative (monoethanolamine, diethanolamine, triethanolamine, etc.);

saturated or unsaturated $C_8$–$C_{20}$, preferably $C_{12}$–$C_{16}$, fatty acid salts, N-acyl N-alkyltaurates, alkyl isethionates, alkyl succinamates, alkyl sulfosuccinates, sulfosuccinate monoesters or diesters and N-acyl sarcosinates.

NONIONIC SURFACTANTS polyoxyalkylenated (polyoxyethylenated, polyoxypropylenated or polyoxybutylenated) alkyl phenols in which the alkyl substituent is $C_6$–$C_{12}$ and containing from 5 to 25 oxyalkylene units; examples which may be mentioned are the products Triton X-45, X-114, X-100 or X-102;

glucosamide, glucamide;

glycerolamides derived from N-alkylamines (U.S. Pat. No. 5,223,179 and FR 1 585 966);

polyoxyalkylenated $C_8$–$C_{22}$ aliphatic alcohols containing from 1 to 25 oxyalkylene (oxyethylene or oxypropylene) units; examples which may be mentioned are the products Tergitol 15-S-9, Tergitol 24-L-6 NMW, Neodol 45-9, Neodol 23-65, Neodol 45-7, Neodol 45-4 and Kyro EOB;

products resulting from the condensation of ethylene oxide with a hydrophobic compound resulting from the condensation of propylene oxide with propylene glycol, such as the Pluronic products;

products resulting from the condensation of ethylene oxide the compound resulting from the condensation of propylene oxide with ethylene diamine, such as the Tetronic products;

amine oxides such as ($C_{10}$–$C_{18}$)alkyldimethylamine oxides and ($C_8$–$C_{22}$)alkoxyethyldihydroxyethylamine oxides;

the alkylpolyglycosides described in U.S. Pat. No. 4,565,647;

oxyalkylenated derivatives of fatty alcohols, such as the Plantaren® products;

$C_8$–$C_{20}$ fatty acid amides;

ethoxylated fatty acids;

ethoxylated fatty amides;

ethoxylated amines.

AMPHOTERIC AND ZWITTERIONIC SURFACTANTS alkyldimethylbetaines, alkylamidopropyldimethylbetaines and alkyltrimethylsulfobetaines;

alkyl amphoacetates or alkyl amphodiacetates, such as the products of the Miranol® range;

the products of condensation of fatty acids with proteins or protein hydrolysates;

amphoteric alkylpolyamine derivatives such as Amphionic XL®, Ampholac 7T/X® and Ampholac 7C/X®.

The formulations can contain other additives, such as:

VISCOSITY MODIFIERS, such as:

cellulose derivatives such as carboxymethylcellulose or hydroxyethylcellulose;

guar derivatives such as hydroxypropylguar, carboxymethylguar or carboxymethylhydroxypropylguar.

HYDROTROPIC AGENTS:

$C_2$–$C_8$ short alcohols, in particular ethanol, but also methanol, propanol and isopropanol;

diols and glycols such as propanediol, ethylene glycol, diethylene glycol or dipropylene glycol. It should be noted that the amphoteric surfactants can also act as hydrotropic agents, as can toluenesulfonate, xylenesulfonate and urea.

MOISTURIZERS OR SKIN PROTECTORS, such as:

glycerol;

urea;

proteins or protein hydrolysates;

cationic polymers such as cationic guar derivatives (Jaguar C13S®, Jaguar C162® or Hicare 1000®.

OTHER ADDITIVES such as:

bactericides or disinfectants such as triclosan;

buffers;

fragrances;

pigments, dyes;

preserving agents.

As more particularly regards the formulations intended for washing laundry by hand (liquid or solid formulations), these formulations can comprise, besides the foam protector according to the invention, the following elements:

SURFACTANTS, in an amount corresponding to about 3–40% by weight relative to the detergent composition. The lists of surfactants which were given for the household detergency formulations remain valid and will not be repeated here. Reference may thus be made thereto.

BUILDERS, in an amount corresponding to about 5–50%, preferably to about 5–30%, by weight for the liquid detergent formulations, or to about 10–80%, preferably 15–50%, by weight for the powdered detergent formulations, such as:

Inorganic Builders:

polyphosphates (tripolyphosphates, pyrophosphates, orthophosphates or hexametaphosphates) of alkali metals, of ammonium or of alkanolamines;

tetraborates;

silicates, in particular those with an $SiO_2/Na_2O$ ratio from about 1.6/1 to 3.2/1 and the lamellar silicates described in U.S. Pat. No. 4,664,839;

alkali metal or alkaline-earth metal carbonates (bicarbonates, sesquicarbonates);

cogranulates of alkali metal silicate hydrates and of alkali metal (sodium or potassium)-carbonates which are rich in silicon atoms, in Q2 or Q3 form, described in EP 488 868;

crystalline or amorphous alkali metal (sodium or potassium) or ammonium aluminosilicates, such as zeolites A, P, X, etc.; zeolite A with particle sizes of about 0.1–10 micrometers is preferred.

Organic Builders:

water-soluble polyphosphonates (ethane 1-hydroxy-1,1-diphosphonates, methylene diphosphonate salts, etc.);

water-soluble salts of carboxylic polymers or copolymers or water-soluble salts thereof, such as:

polycarboxylate ethers (oxydisuccinic acid and its salts, tartaric acid and its salts, succinic acid and its salts, or co-products thereof);

hydroxypolycarboxylate ethers;

citric acid and its salts, mellitic acid and succinic acid, and salts thereof;

polyacetic acid salts (ethylenediaminetetraacetates, nitrilotriacetates, N-(2-hydroxyethyl)nitrilodiacetates);

$C_5$–$C_{20}$ alkylsuccinic acids and salts thereof (2-dodecenylsuccinates, lauryl succinates);

polycarboxylic acetal esters;

polyaspartic acid, polyglutamic acid and salts thereof;

polyimides derived from the polycondensation of aspartic acid and/or glutamic acid;

polycarboxymethyl derivatives of glutamic acid or of other amino acids.

ANTI-SOILING AGENTS, in an amount of about 0.01–10%, preferably about 0.1–5% and most particularly of about 0.2–3% by weight, such as:

cellulose derivatives such as cellulose hydroxy ethers, methylcellulose, ethylcellulose, hydroxypropylmethylcellulose or hydroxybutylmethylcellulose;

polyvinyl ethers grafted onto polyalkylenated trunks, such as polyvinyl acetates grafted onto polyoxyethylene trunks (EP 219 048);

polyvinyl alcohols;

polyester copolymers based on ethylene terephthalate and/or propylene terephthalate and polyoxyethylene terephthalate units, with an ethylene terephthalate and/or propylene terephthalate (number of units)/polyoxyethylene terephthalate (number of units) molar ratio from about 1/10 to about 10/1, preferably from about 1/1 to about 9/1, the polyoxyethylene terephthalates containing polyoxyethylene units with a molecular weight from about 300 to about 5000, preferably from about 600 to about 5000 (U.S. Pat. Nos. 3,959,230, 3,893,929, 4,116,896, 4,702,857, 477,066);

sulfonated polyester oligomers obtained by sulfonation of an oligomer derived from ethoxylated allylic alcohol, from dimethyl terephthalate and from 1,2-propylene diol, containing from 1 to 4 sulfonated groups (U.S. Pat. No. 4,968,451);

polyester copolymers based on propylene terephthalate and polyoxyethylene terephthalate units and ending with ethyl or methyl units (U.S. Pat. No. 4,711,730) or polyester oligomers ending with alkylpolyethoxy groups (U.S. Pat. No. 4,702,857) or sulfopolyethoxy (U.S. Pat. No. 4,721,580) or sulfoaroyl (U.S. Pat. No. 4,877,896) anionic groups;

polyester-polyurethanes obtained by reacting polyesters with a number-average molecular mass of 300–4000 obtained from adipic acid and/or terephthalic acid and/or sulfoisophthalic acid and from a diol with a mass of less than 300, with a prepolymer containing isocyanate end groups obtained from a polyoxyethylene glycol with a molecular mass of 600–4000 and from a diisocyanate (FR 2 334 698).

ANTI-REDEPOSITION AGENTS, more particularly in formulations intended for washing laundry, in an amount of about 0.01–10% by weight for a powdered detergent composition, and of about 0.01–5% by weight for a liquid detergent composition, such as:

ethoxylated monoamines or polyamines, and ethoxylated amine polymers (U.S. Pat. No. 4,597,898, EP 11984);

carboxymethylcellulose;

sulfonated polyester oligomers obtained by condensation of isophthalic acid, dimethyl sulfosuccinate and diethylene glycol (FR 2 236 926);

polyvinylpyrrolidones.

CHELATING AGENTS for chelating calcium, magnesium and iron, in an amount of about 0.1–10%, preferably of about 0.1–3%, by weight, such as;

aminocarboxylates such as ethylenediaminetetraacetates, hydroxyethyl ethylenediaminetriacetates and nitrilotriacetates;

aminophosphonates such as nitrilotris(methylene phosphonates);

polyfunctional aromatic compounds such as dihydroxydisulfobenzenes.

POLYMERIC DISPERSANTS, in an amount of about 0.1–7% by weight, to control the calcium and magnesium hardness, such as:

water-soluble polycarboxylic acid salts with a molecular mass from about 2000 to about 100,000, obtained by polymerization or copolymerization of ethylenically unsaturated carboxylic acids such as acrylic acid, maleic acid or anhydride, fumaric acid, itaconic acid, aconitic acid, mesaconic acid, citraconic acid or methylenemalonic acid, and most particularly polyacrylates with a molecular mass from about 2000 to about 10,000 (U.S. Pat. No. 3,308,067), copolymers of acrylic acid and of maleic anhydride with a molecular mass from about 5000 to about 75,000 (EP 66915);

FLUORESCERS, in an amount of about 0.05–1.2% by weight, such as:

stilbene, pyrazoline, coumarin, fumaric acid, cinnamic acid, azoles, methinecyanin, thiophene, etc. derivatives ("The production and application of fluorescent brightening agents"—M. Zahradnik, published by John Wiley & Sons, New York-1982-).

SOFTENERS, in an amount of about 0.5–10% by weight, such as clays.

ENZYMES in an amount which can be up to 5 mg by weight, preferably about 0.05–3 mg, of active enzyme/g of detergent composition, such as:

proteases, amylases, lipases, cellulases and peroxidases (U.S. Pat. Nos. 3,553,139, 4,101,457, 4,507,219, 4,261,868).

OTHER ADDITIVES such as:

alcohols (methanol, ethanol, propanol, isopropanol, propanediol, ethylene glycol, glycerol);

buffers;

fragrances;

pigments.

The foam protector according to the invention can likewise form part of the composition of cosmetic formulations such as, inter alia, hair or body shampoo formulations, body or facial cleansing gels, liquid soaps and bubble bath compositions.

Besides the agent according to the invention, said formulations can comprise at least one of the following elements:

SURFACTANTS, of anionic type, where appropriate combined with nonionic, zwitterionic and amphbteric surfactants, in an amount ranging from 0.05 to 20% of the weight of the preparation. In this case also, reference may be made to the lists of surfactants given previously.

WETTING AGENTS, such as:

glycerol, sorbitol;

urea;

collagen, gelatin;

aloe vera;

hyaluronic acid.

EMOLLIENTS, such as:

alkylmonoglycerides, alkyldiglycerides and triglycerides, such as oils extracted from plants and vegetation (palm oil, coconut oil, cotton seed oil, soybean oil, sunflower oil, olive oil, grape seed oil, sesame oil, groundnut oil, castor oil, etc.) or oils of animal origin (tallow, fish oils, etc.), derivatives of these oils, such as hydrogenated oils, lanolin derivatives, mineral oils or liquid paraffins, perhydrosqualane, squalene;

diols such as 1,2-propanediol, 1,3-butanediol, cetyl alcohol, stearyl alcohol, oleyl alcohol, polyethylene glycols or polypropylene glycols;

fatty esters such as isopropyl palmitate, 2-ethylhexyl cocoate, myristyl myristate or lactic acid esters, stearic acid, behenic acid, isostearic acid, silicone oils combining cyclic polydimethylsiloxanes, $\alpha,\omega$-hydroxylated polydimethylsiloxanes, $\alpha,\omega$-trimethylsilyl polydimethylsiloxanes, polyorganosiloxanes such as polyalkylmethylsiloxanes, polymethylphenylsiloxanes, polydiphenylsiloxanes, aminosilicone derivatives, silicone waxes, copolyether silicones (such as the oil Silbione 70646® or DC 190®) or mixed silicone derivatives such as polyalkylmethylsiloxane-silicone copolyether mixed copolymers.

MINERAL PARTICLES OR SUNSCREENS, such as:

calcium carbonate, inorganic oxides in powder form or in colloidal form (particles of less than or about one micrometer in size, occasionally a few tens of nanometers) such as titanium dioxide, silica, aluminum salts, kaolin, talc, clays and derivatives thereof, etc.

PRESERVING AGENTS, in an amount from about 0.01 to about 3% by weight, such as:

methyl, ethyl, propyl and butyl esters of p-hydroxybenzoic acid, sodium benzoate, Germaben®.

As alternatives to these chemical agents, agents which modify the water activity and which greatly increase the osmotic pressure can occasionally be used, such as carbohydrates or salts.

VISCOSITY MODIFIERS/GELLING AGENTS, such as:

Carbopol® crosslinked polyacrylates;

cellulose derivatives such as hydroxypropylcellulose, carboxymethylcellulose;

guars and derivatives thereof, carob, tara gum or cassia gum;

xanthan gum;

alginates, carrageenans;

chitin derivatives such as chitosan.

The foam protector according to the invention can similarly be used in cleansing bar formulations known as toiletry soaps or general purpose soaps.

Conventional cleansing bar compositions generally comprise fatty acid salts used in combination with the agent according to the invention, but also surfactants other than fatty acid salts or the fatty acids themselves, which are mentioned previously.

These compositions can even contain no fatty acid or fatty acid salt, and in this case their formulations are based on other surfactants such as, for example, sodium $C_8$–$C_{22}$ alkyl isethionates or sodium $C_8$–$C_{22}$ alkyl sulfates.

AGENTS FOR REDUCING SKIN IRRITATION/MOISTURIZERS alkali metal salts or isethionates;

carbohydrates (glycerol or sorbitol for example);

polyethylene glycols or polypropylene glycol;

alkoxylated sugar derivatives or derivatives thereof (for example methyl glucose);

water-soluble or water-dispersible polymers such as collagen or certain non-allgergenic derivatives of animal or plant proteins (for example wheat protein hydrolysates);

natural hydrocolloids (guar gum, carob gum, tara gum, etc.) or hydrocolloids derived from fermentation processes, such as xanthan gum, and derivatives of these polycarbohydrates such as modified celluloses (for example hydroxyethylcellulose, carboxymethylcellulose or cationic celluloses such as the products Polymer JR®), guar or carob derivatives such as cationic derivatives thereof (Jaguar C13S®, Jaguar C162®) or nonionic derivatives (for example hydroxypropylguar), anionic derivatives (carboxymethylguar) or nonionic/anionic mixed derivatives such as carboxyhydroxypropylguars or nonionic/cationic mixed derivatives. Synthetic polymers such as polyacrylates or synthetic cationic polymers, known under the CTFA generic name "Polyquaternium", for example the polymers Mirapol A15® or Mirapol 550®, can also be added alternatively or in combination.

SEQUESTERING AGENTS for sequestering calcium, such as citrate ions.

EMOLLIENTS such as silicones or oils or fatty substances used in this respect in the cosmetics industry (mineral oils, fatty acid esters, triglycerides, silicones, etc.).

ADDITIVES fragrances, dyes and/or opacifiers such as pigments (titanium oxide particles);

bactericides or fungicides.

In a cleansing bar whose formulation consists mainly of soaps of monocarboxylic fatty acids (sodium, potassium, mono-, di- or triethanolammonium salts), the fatty acid contents of the soaps are generally more than 25% by weight of the formulation, generally from 30 to 95% by weight.

In a cleansing bar whose formulation is based on main constituents other than fatty acid soaps, from 0 to 50% by weight, preferably from 1 to 40% by weight, of these fatty acid soaps are found in the formulation.

These cleansing bar compositions can also contain from 0 to 95%, preferably from 0 to 60%, of surfactants other than soaps, in particular $C_8$–$C_{22}$ alkyl or alkenyl isethionates, as well as alkyl ether sulfates, alkylbetaines, alkylamidopropylbetaines, alkylampho-acetates, -diacetates, -propionates or -dipropionates used to reduce the irritation which may be caused by the other surfactants, mainly the anionic surfactants.

From 1 to 15% of $C_8$–$C_{22}$ free fatty acids can also be introduced into the soap compositions as overfatting agents or to modify the appearance and the creamy nature of the foam during washing.

Waxes such as paraffin waxes, natural waxes such as beeswax or ozokerites or silicone waxes can also be found in these compositions. These waxes are advantageously used to improve the appearance, behavior, processibility and conservation on storage of the cleansing bars.

The shampoos, and more generally the detergent compositions for personal-hygiene use, can contain, besides the foam protector according to the invention, the common additives present in formulations of this type.

Mention May be Made in Particular of:

SURFACTANTS such as those indicated previously, in an amount ranging from 5 to 25%.

CONDITIONERS such as:

synthetic cationic polymers such as Mirapol AD1® or Mirapol A550®, natural cationic polymers such as cationic guar derivatives (Jaguar C135®, Jaguar C162®) or cationic cellulose derivatives (Polymer JR400®);

polyorganosiloxanes used in their native form or dissolved in a common solvent therefor (silicone oils of low mass, highly branched liquid paraffins, fatty esters such as, for example, isopropyl palmitate, etc.).

ANTIDANDRUFF AGENTS, such as:

pyridinethiones, more especially zinc pyridinethione, selenium-based compounds such as selenium sulfide or Octopyrox®.

AGENTS FOR MODIFYING THE APPEARANCE OR THE VISCOSITY, such as:

pearlescent compounds based on polyethylene glycol stearate;

the Carbopol® products, hydrocolloids and derivatives thereof, such as guar or modified guars, carob, xanthan gum and cellulose derivatives (hydroxyethylcellulose, carboxymethylcellulose).

OTHER ADDITIVES, such as:

anti-parasitic (anti-louse) agents, such as Lindane or various pyrethrins;

dyes, pigments;

fragrances.

Concrete but nonlimiting examples of the invention will now be given.

EXAMPLE 1

The subject of this example is the preparation of a copolymer based on acrylic acid and on ethylene oxide.

10 g of sodium hydroxide are dissolved in 680 g of water, at room temperature, in a 2 liter glass reactor equipped with a jacket and a stirrer (190 rpm). The temperature is then increased to 65° C.

An initiator solution comprising 0.105 g of ammonium persulfate and 30 g of water is prepared.

Separately, a solution comprising 30 g of water and 70 g of acrylic acid and a solution comprising 10 g of sodium hydroxide and 30 g of water are mixed.

14 g of polyethylene oxide (100,000 g/mol) are dissolved in the reactor. Next, the solution comprising the acrylic acid and the initiator solution are introduced continuously. The operation is carried out over 300 minutes, while maintaining a constant rate of introduction and keeping the temperature at 65° C.

Once the introduction is complete, the reaction mixture is left stirring for 120 minutes at 65° C.

The mixture is finally cooled to room temperature.

A copolymer is obtained in which the polyoxyethylenated chain bears grafts of polyacrylic acid type.

The pH is 4.8.

The solids content is 12%.

EXAMPLE 2

The subject of this example is the preparation of a copolymer based on acrylic acid and on ethylene oxide/propylene oxide.

10 g of sodium hydroxide are dissolved in 630 g of water, at room temperature, in a 2 liter glass reactor equipped with a jacket and a stirrer (190 rpm). The temperature is then increased to 65° C.

An initiator solution comprising 0.46 g of ammonium persulfate and 10 g of water is prepared.

Separately, a solution comprising 28 g of water and 92 g of acrylic acid is prepared.

18.4 g of a polyethylene oxide/polypropylene oxide dibloc copolymer (6500 g/mol, 50% ethylene oxide) and 180 g of ethanol are introduced into the reactor.

Next, the initiator solution is added once the dibloc copolymer has dissolved.

The solution comprising the acrylic acid is then added continuously, over a period of 120 minutes, while maintaining a constant rate of introduction and keeping the temperature at 65° C.

Once the introduction is complete, the reaction mixture is left stirring for 120 minutes at 65° C.

The mixture is finally cooled to room temperature.

A copolymer is obtained whose polyoxyethylenated/polyoxypropylenated chain bears grafts of polyacrylic acid type.

The pH is 4.8.

The solids content is 12%.

EXAMPLE 3

This example illustrates the preparation of a copolymer comprising vinyl acetate, acrylic acid, butyl acrylate and sodium sulfoethyl methacrylate as monomers.

A mixture comprising 150.6 g of water, 1.6 g of sodium lauryl sulfate, 7.21 g of an aqueous solution of 44.35% sodium sulfoethyl methacrylate and 1.6 g of sodium acetate is introduced into a 2 liter glass reactor equipped with a jacket and a stirrer (190 rpm), and the reactor is brought to 70° C.

An initiator solution comprising 1.6 g of ammonium persulfate and 6 g of water is prepared and is introduced into the reactor at t=to.

A mixture comprising 150 g of water, 246.4 g of vinyl acetate, 51.2 g of butyl acrylate, 22.4 g of acrylic acid and 1.6 g of sodium lauryl sulfate is emulsified. The emulsion is then added to the reactor over a period of 5 hours starting from to.

The following are then added:

a solution of 2.176 g of sodium sulfoxide and 1.6 g of sodium bicarbonate in 48 g of water, over 7 hours starting from to;

a solution of 1.83 g of tert-butyl hydroperoxide (70%) and 40 g of water, over 7 hours starting from to.

The temperature is then increased to 80° C. and maintained for one hour before cooling.

A random copolymer is obtained.

EXAMPLE 4

This example illustrates the preparation of a copolymer comprising acrylic acid and 2-hydroxyethyl methacrylate.

10 g of sodium hydroxide dissolved in 252 g of water are introduced, at room temperature, into a 2 liter glass reactor equipped with a jacket and a stirrer (190 rpm).

The temperature is then increased to 65° C.

A mixture of 408 g of water, 55 g of 2-hydroxyethyl methacrylate, 55 g of acrylic acid and 0.22 g of methyl mercaptopropionate is prepared.

A solution comprising 1.1 g of ammonium persulfate is introduced into the reactor. The above mixture is then added continuously over a period of 120 minutes, at a temperature of 65° C.

Once the introduction is complete, the reaction mixture is left stirring for 120 minutes at 65° C.

The mixture is finally cooled to [lacuna] temperature.

A copolymer with a random distribution of monomers is obtained.

The pH is 7.2.

The solids content is 15.3%.

EXAMPLE 5

The subject of this example is the use of each of the copolymers obtained above in a detergent formulation, in the presence of grease.

The detergent formulation used comprises:
- 21% by dry weight of sodium lauryl ether sulfate (Empicol ESB/3M sold by Albright & Wilson);
- 3% by dry weight of ethoxylated alcohol containing on average 6 oxyethylene units (Rhodasurf IDO60 sold by Rhodia Chimie);
- 3% by dry weight of cocoamidopropylbetaine (Dehyton K sold by Henkel);
- qs 100% by weight of water.

The pH was adjusted to 7.

The copolymers obtained previously were tested separately with the formulation described above, the copolymer content being 2% by weight relative to that of the formulation, and the whole being diluted to 1%.

The test consists in carrying out the following:
- 250 ml of the formulation described previously are introduced into a 500 ml flask and 7 ml of grease (50/50 by weight mixture of sunflower oil and margarine) are added.

The flask is stoppered and is then subjected to series of upturning, at an upturning rate of 60 turns per minute.

The results show that the volume of foam maintained in the presence of the grease used remains about 15% higher in the case of formulations comprising the copolymer according to the invention, than that of a formulation not containing it.

What is claimed is:

1. A method of conserving foams generated be a foam forming formulation, comprising the step of adding to said formulation, an effective foam conserving amount of a copolymer or a mixture of copolymers comprising:
   at least one monomer (I) which is a $C_3$–$C_5$ unsaturated acid, a diacid or an anhydride,
   at least one monomer (II) which is ethylene oxide or propylene oxide,
   at least one monomer (III) which is a linear or branched $C_4$–$C_8$ hydrocarbon comprising at least one ethylenic unsaturation,
   at least one monomer (IV) which is vinyl acetate; alkyl acrklate; alkyl methacrylate; alkyl methacrylate or acrylate bearing a sulfoalkyl group, in the form of an acid or of an alkali metal salt or ammonium salt of formula: —$N(R^3)_3{}^+$, wherein $R^3$, which are identical or different, represent a hydrogen atom or $C_1$–$C_4$ hydrocarbon radical, optionally substituted with a hydroxyl group; hydroxyalkyl acrylate; or hydroxyalkyl methacrylate, said alkyl radical being methyl, ethyl, propyl, prropyl isomer, butyl, or butyl isomer,said copolmer comprising at least one monomer (I) and at least one monomer (IV), and having the following composition: 1–15% of monomer (I); 50–85% of vinyl acetate; 5–20% of alkyl acrylate or methacrylate; 0.5–5% of sodium sulfoalkyl acrylate or methacrylate; and the sum of each of the monomers used being equal to 100% relative to the weight of the copolymer.

2. A method according to claim 1, wherein the monomer (I) is acrylic acid or methacrylic acid.

3. A method according to claim 1, wherein the monomer (IV) is 2-hydroxyethyl acrylate, or 2-hydroxyethyl methacrylate and the monomer (I) is acrylic acid, or methacrylic acid.

4. A method according to claim 1, wherein the proportion of monomer (I) relative to the monomer (IV) is between 0.1 and 90% by weight relative to the weight of the copolymer.

5. A method according to claim 1, wherein the amount of the copolymer represents 0.05 to 10% by weight of the formulation.

6. A method according to claim 5, wherein the amount of foam protector copolymer represents 0.05 and 2% by weight.

7. A method according to claim 1, wherein the formulation is a detergent formulation for washing up kitchenware by hand or washing laundry by hand.

* * * * *